(12) United States Patent
Mueller

(10) Patent No.: US 12,364,592 B2
(45) Date of Patent: Jul. 22, 2025

(54) INTRAOCULAR LENS HAVING A SPECIFIC, THREE-DIMENSIONALLY CURVED HAPTIC ELEMENT

(71) Applicant: Carl Zeiss Meditec AG, Jena (DE)

(72) Inventor: Stephanie Mueller, Neuruppin (DE)

(73) Assignee: Carl Zeiss Meditec AG, Jena (DE)

( * ) Notice: Subject to any disclaimer, the term of this patent is extended or adjusted under 35 U.S.C. 154(b) by 743 days.

(21) Appl. No.: 17/683,172

(22) Filed: Feb. 28, 2022

(65) Prior Publication Data

US 2022/0183820 A1 Jun. 16, 2022

Related U.S. Application Data

(63) Continuation of application No. PCT/EP2020/072215, filed on Aug. 7, 2020.

(30) Foreign Application Priority Data

Aug. 30, 2019 (DE) ...................... 10 2019 123 295.3

(51) Int. Cl.
*A61F 2/16* (2006.01)

(52) U.S. Cl.
CPC ........ *A61F 2/161* (2015.04); *A61F 2002/169* (2015.04); *A61F 2002/16901* (2015.04); *A61F 2230/0095* (2013.01)

(58) Field of Classification Search
CPC .... A61F 2/16; A61F 2230/0095; A61F 2/161; A61F 2002/169; A61F 2002/16901; A61F 2002/1683; A61F 2002/1681; A61F 2/14
See application file for complete search history.

(56) References Cited

U.S. PATENT DOCUMENTS

| 4,077,071 A | 3/1978 | Freeman |
| 4,134,161 A | 1/1979 | Bayers |

(Continued)

FOREIGN PATENT DOCUMENTS

| DE | 10016929 A1 | 10/2001 |
| DE | 69828477 T2 | 12/2005 |

(Continued)

OTHER PUBLICATIONS

International Preliminary Report on Patentability of the European Patent Office in PCT/EP2020/072215 (from which this application claims priority) mailed Mar. 10, 2022 and English language translation thereof.

(Continued)

*Primary Examiner* — Jerrah Edwards
*Assistant Examiner* — Hanna L Pasqualini
(74) *Attorney, Agent, or Firm* — Ewers IP Law PLLC; Falk Ewers

(57) ABSTRACT

An intraocular lens is provided which includes a single optical part, a haptic element, which is coupled to the optical part, and an optical main axis, which penetrates a front face and a rear face of the optical part, the haptic element having a first haptic part, which is in the form of a first ring and extends around the optical part, and at least one second haptic part, which is in the form of a second ring and extends around the optical part and is elastically movable relative to the first haptic part, at least one of the two rings being uneven in the peripheral direction about the optical main axis, at least one of the two rings having exactly two ring valleys and exactly two ring hills.

11 Claims, 2 Drawing Sheets

(56) References Cited

U.S. PATENT DOCUMENTS

| | | | |
|---|---|---|---|
| 4,338,687 A | 7/1982 | Rainin | |
| 4,804,361 A | 2/1989 | Anis | |
| 6,027,531 A | 2/2000 | Tassignon | |
| 8,043,372 B2 | 10/2011 | Bumbalough | |
| 9,713,526 B2 | 7/2017 | Rombach | |
| 2004/0111152 A1 | 6/2004 | Kelman | |
| 2005/0113914 A1 | 5/2005 | Miller et al. | |
| 2007/0100444 A1 | 5/2007 | Brady et al. | |
| 2007/0106381 A1* | 5/2007 | Blake | A61F 2/1694 623/6.37 |
| 2011/0313523 A1 | 12/2011 | Hayes | |
| 2013/0053955 A1 | 2/2013 | Currie | |
| 2014/0277437 A1* | 9/2014 | Currie | A61F 2/1624 623/6.37 |
| 2015/0142108 A1* | 5/2015 | Akura | A61F 2/1629 623/6.37 |
| 2016/0310263 A1 | 10/2016 | Akura | |
| 2017/0312071 A1 | 11/2017 | Ghabra et al. | |

FOREIGN PATENT DOCUMENTS

| | | |
|---|---|---|
| DE | 10310961 B4 | 12/2006 |
| DE | 102007057122 A1 | 6/2008 |
| EP | 2099388 B1 | 11/2017 |
| GB | 2518378 A | 3/2015 |
| JP | S51151149 A | 12/1976 |
| JP | 4486122 B2 | 6/2010 |
| JP | 2014221084 A | 11/2014 |
| JP | 2015131104 A | 7/2015 |
| WO | 2014058316 A1 | 4/2014 |

OTHER PUBLICATIONS

International Search Report dated Oct. 22, 2020 of international application PCT/EP2020/072215 on which this application is based.
Office Action dated Apr. 11, 2023, issued in Japanese counterpart application No. 2022-512394 and English Language translation thereof.
Office Action issued in German Patent Application No. DE 10 2019 123 295.3 (from which this application claims priority), dated Jul. 10, 2020 and English language translation thereof.
Office Action issued in Indian Application No. IN 202217017982, dated Sep. 7, 2022 and English language translation thereof.
U.S. Appl. No. 17/683,202, filed Feb. 28, 2022, Stephanie Mueller.

* cited by examiner

INTRAOCULAR LENS HAVING A SPECIFIC, THREE-DIMENSIONALLY CURVED HAPTIC ELEMENT

CROSS REFERENCE TO RELATED APPLICATIONS

This application is a continuation application of international patent application PCT/EP2020/072215, filed Aug. 7, 2020, designating the United States and claiming priority to German patent application 10 2019 123 295.3, filed Aug. 30, 2019, and the entire content of both applications is incorporated herein by reference.

TECHNICAL FIELD

One aspect of the disclosure relates to an intraocular lens including a single optical part and including a haptic coupled to the optical part, and having a main optical axis which passes through a front side and a back side of the optical part, the haptic including a first haptic part which is in the form of a first ring and encircles the optical part, and at least one second haptic part which is in the form of a second ring and encircles the optical part and which is elastically movable relative to the first haptic part, at least one of the two rings having an uneven form in the circumferential direction about the main optical axis.

BACKGROUND

Intraocular lenses are known in various embodiments. Typically, intraocular lenses have at least two separate haptics formed opposite one another in the circumferential direction around the main optical axis and formed so as to radially adjoin the optical part. It is also possible for more than two such separate haptics to be formed, for example three haptics.

Intraocular lenses may be implanted in place of a natural lens of the eye at different defined positions within the eye. It is thus envisaged in this context that specific intraocular lenses are implanted in an anterior chamber of the eye. For example, such anterior chamber lenses may be fixed in the anterior iridocorneal angle.

There are also known intraocular lenses that are referred to as iris clip lenses. Such intraocular lenses are secured to the pupil. In particular, they are clipped to the pupil opening. Such an intraocular lens is known, for example, from DE 10 2007 057 122 A1. The intraocular lens therein, with this specific implantation site in the eye, has two opposite haptics. Each of these haptics has two L-shaped haptic arms. Mutually facing ends of these haptic arms, viewed in a plane at right angles to the main optical axis of this intraocular lens, are arranged so as to face one another, but arranged contactlessly and without overlap. With haptic arms formed in this way, the gap formed in the circumferential direction around the main optical axis between the ends of the haptic arms can be used to clip onto the iris. However, such lenses are not intended for and not suitable for implantation in a capsular bag of an eye.

In this regard, there are further known specific intraocular lenses that can be referred to as posterior chamber lenses and are implanted into a capsular bag of the eye.

DE 103 10 961 B4 discloses an intraocular lens which is a posterior chamber lens. In this posterior chamber lens, two separate haptics are formed radially adjoining the optical part in opposite regions of the optical part. Both the respective haptics are formed with two haptic parts. The two haptic parts of a haptic are movable relative to one another. For this purpose, at a defined connection site between the haptic parts connected to one another in one-piece form, a defined kink point is formed, for example in the form of an integral hinge. In this way, the radially outer haptic part of this haptic can be folded or pivoted relative to the first haptic part that directly adjoins the optical part. This pivoting motion is possible only in the plane at right angles to the optical axis. This is intended to reduce the radial width of the overall intraocular lens there in order to be able to avoid irritation in the interior of the capsular bag resulting from these haptics.

Such posterior chamber lenses have a more or less planar structure. As a consequence, the capsular bag, which shrinks following the implantation, comes into contact with the back side of the optical part. There can be a migration of cells in the contact area, and so the posterior capsular bag may opacify. It is known that such an opacification of the posterior capsular bag can be avoided, or at least reduced, if the back side of the optical part of the intraocular lens is rinsed by aqueous humor. This requires a distance to be present between this back side of the optical part of the intraocular lens and the posterior capsular bag.

Maintaining a distance between a back side of the optical part of the intraocular lens and the capsular bag when the intraocular lens is in the implanted state in the capsular bag is not possible in DE 103 10 961 B4. Therefore, the aforementioned problem is not solved by this posterior chamber lens either.

US 2007/0100444 A1 describes an intraocular lens having a three-dimensionally formed haptic in the form of a braid. The haptic has a plurality of arches which bulge radially with respect to the main optical axis. With their two ends, these arches are arranged at different positions in the direction of the main optical axis of the intraocular lens. One end of the arches is arranged at a circumferential side of the optical part of the intraocular lens in considered fashion. The second end of the arches is fastened so as to project beyond the optical part in the axially forward direction and fastened to an annulus of the haptic. The annulus is completely arranged in a flat plane which is arranged at a distance from the optical part and oriented at right angles to the optical axis of the lens.

U.S. Pat. No. 8,043,372 B2 has disclosed an intraocular lens which likewise has a three-dimensionally formed haptic, the shape of which does not extend in a plane. In one exemplary embodiment, this haptic has two rings that encircle the main optical axis. Each of these rings is wavy in meandering fashion. The meandering shape with its many loops is designed so as to encircle the main optical axis. The two rings are interconnected at inflection points of the waves, with the ring peaks radially further to the inside being freely protruding and facing one another or facing the main optical axis.

Such three-dimensional haptics are intended to improve the secure hold of the intraocular lens in the capsular bag. However, these haptics have very complex forms and are therefore difficult to produce. The complexity of form also renders the implantation of the intraocular lens into the capsular bag more difficult. Moreover, these haptics also have the problem that in a capsular bag they are subject to significant radial compression in regions on account of their symmetry about the main optical axis.

SUMMARY

It is an object of the present disclosure to provide an intraocular lens which facilitates improved positioning in a capsular bag of an eye.

This object is achieved with an artificial intraocular lens as described herein.

One aspect of the disclosure relates to an artificial intraocular lens with a single optical part. The optical part is a lens. The optical part has specific optical imaging properties such that specific corrections of visual defects can be implemented therewith.

Moreover, the intraocular lens includes a haptic which is coupled to the optical part. The intraocular lens has an optical axis or a main optical axis, which passes through a front side and a back side of the optical part and in particular passes through these centrally in the middle region. The haptic has a first haptic part which is in the form of a first ring. The first ring is formed to encircle the optical part. The haptic has at least one second haptic part which is in the form of a second ring. The second ring is formed to encircle the optical part. The two haptic parts are elastically movable. At least one of the two rings has an uneven form in the circumferential direction when considered about the main optical axis. This means that the ring, when viewed along its longitudinal axis and hence when considered along its ring shape, is not formed in a plane but has an uneven profile in this respect. At least one of the two rings has exactly two ring valleys and exactly two ring peaks. A relatively simple geometry of this at least one haptic part is formed by such an embodiment. This has advantages from a manufacturing point of view. Moreover, the mount of the intraocular lens in the capsular bag is improved by such an embodiment. In particular, it is possible to at least reduce both an unwanted rotation of the intraocular lens in the capsular bag and an unwanted tilt of the optical part. This can facilitate improved fixation of the position of the intraocular lens in the capsular bag. In relation to the exactly two ring valleys and the exactly two ring peaks, this designation of height is considered in relation to a central plane of the optical part. This central plane is oriented at right angles to the main optical axis and, in particular, runs centrally through the optical part. The ring valleys are arranged closer to this central plane than the ring peaks.

Moreover, being able to also position the intraocular lens more securely in its position in the axial direction, and hence in the direction of the main optical axis, within the capsular bag is also rendered possible by such an embodiment.

In an advantageous embodiment, provision is made for the at least one ring with the exactly two ring valleys and the exactly two ring peaks to have the shape of an edge ring or a boundary of a saddle form. This means that, proceeding from a saddle form, the ring in this respect as it were represents a border or an edge of such a saddle form. Consequently, this ring may also be referred to as saddle form edge ring. This specification also specifies the configuration with two ring valleys and exactly two ring peaks.

The shape of this ring with the exactly two ring valleys and exactly two ring peaks can also be understood to the effect of a ring formed in a plane being curved about an axis at right angles to the main optical axis so that this three-dimensional shape of the ring arises. This axis about which this ring is curved runs in the central plane of the optical part in particular.

By this specific shape of the at least one ring with the exactly two ring valleys and the exactly two ring peaks it is possible to better take account of the aforementioned advantages. Firstly, this facilitates a very simple structure but, secondly, still facilitates a targeted selective connection to the optical part. This facilitates a great individual deformability of this ring, especially in the region of the ring peaks, but at the same time establishes sufficient mechanical connection to the optical part.

In particular, provision is made for the at least one ring to merge with the optical part with its exactly two ring valleys and for its ring peaks to be arranged so as not to be in contact with the optical part. In particular, the ring with its exactly two ring valleys merges with the optical part at two different positions along the circumferential side. As a result of such a configuration, as it were only two direct mechanical connection points are formed between the ring and the optical part, specifically by way of the two opposing ring valleys. As a result, a symmetric mechanical embodiment of the connection is established between the ring and the optical part. As a result, it is possible to avoid unwanted asymmetric connections to the optical part. The production of the intraocular lens can be simplified as a result of providing for only two mechanical connection points between the ring and the optical part. At the same time, this likewise reduces the complexity of form of the entire intraocular lens.

The intraocular lens can have an integral embodiment. However, provision can also be made for the haptic and the optical part to be separate components. In particular, the haptic can be mechanically connected to the optical part in that case. By way of example, it is possible to form a clamping connection or a plug-in connection or a snap-in connection between an edge region of the optical part and the haptic. By way of example, the haptic may have depressions on the inner side, especially in the ring valleys, an edge region of the optical part engaging in and being held by said depressions. However, a connection by way of adhesive bonding may also be provided.

In an advantageous embodiment, provision is made for the ring valleys to be arranged at a first radius with respect to the main optical axis in the case of a projected view in the direction of the main optical axis and for the ring peaks to be arranged at a second radius which is comparatively larger than the first radius in the case of this projected view. Consequently, in this projected view, the ring in its end position is not formed circularly in the projection plane but is deformed in this respect. In this context, the ring valleys are positioned further to the inside than the ring peaks. Consequently, the ring peaks are radially further away from the main optical axis than the ring valleys. This applies in particular to the observation in the projection plane. This improves the elastic movability of the ring, especially at the ring peaks. Consequently, there can be a more individual fit to the embodiment of the capsular bag and it is consequently possible to obtain an even more finely adjusted and more precise positioning of the intraocular lens in the capsular bag. This deformation specification and these deformation properties are improved even further, especially by these ring peaks projecting radially further to the outside, which are then also embodied as protruding freely from and as not being in contact with the optical part and which have a greater distance from a central plane than the ring valleys when considered in the direction of the main optical axis. On account of this advantage, the deformation fit to very different embodiments of capsular bags may also be improved and, as a result thereof, the improved positioning of the intraocular lens in different capsular bags may be facilitated in turn.

Typically, provision is made for the at least one ring with the exactly two ring valleys and the exactly two ring peaks to have a first ring portion which extends from the first ring valley over a first ring peak and up to the subsequent second ring valley. A clear width of the ring portion as measured between the ring valleys is at least 90 percent of the diameter of the optical part. In particular, this clear width is 100 percent or slightly more than 100 percent of this diameter. Thus, this embodiment creates a ring portion which extends from the first ring valley to the second ring valley with its span and, in this respect, represents a single U-shaped arch. This U-shaped arch therefore surrounds the optical part in a first half-sided circumferential region or encompasses said optical part. In particular, this is also evident in the aforementioned projection plane.

Typically, two successive ring valleys, which immediately follow a ring peak on opposite sides in the direction of the longitudinal axis of the ring, are offset by 180° in the circumferential direction about the main optical axis. Consequently, they are at opposite sides in this azimuthal direction.

Typically, provision is made for the at least one ring with the exactly two ring valleys and the exactly two ring peaks to have a first ring portion which extends from the first ring valley over a first ring peak and up to the subsequent second ring valley, the curvature of the first ring portion being directed radially to the outside in relation to the main optical axis. The direction of curvature of this first ring portion, which represents a half ring, consequently is formed in correspondence with the curvature of the circumference of the optical part, in particular over its entire length. These directions of curvature are therefore directed in the same way but different in terms of magnitude. In particular, a ring portion is formed as an uneven, U-shaped arch. The U-opening faces the main optical axis.

In particular, this relates to the entire arch span between the two adjacent ring valleys of this first ring portion.

Typically, provision is made for the ring peaks to have a greater distance from the central plane of the optical part than the ring valleys when considered in the direction of the main optical axis. In particular, provision is made for the first ring to have the same shape as the second ring. In particular, provision is made for these two rings to be arranged symmetrically with respect to the central plane of the optical part. This means that, in particular, the ring valleys directly abut one another and the ring peaks are arranged at the same azimuthal position in the circumferential direction about the main optical axis in each case and are maximally spaced apart. This means that a distance measured in the direction of the main optical axis varies in the circumferential direction about the main optical axis and is minimal at the positions of ring valleys of these two rings and is maximal at positions of the ring peaks of the two rings.

The optical part has a central thickness in particular. This central thickness is measured along the main optical axis and represents the greatest thickness of the optical part. A thickness of the optical part is formed, which is measured between the maximum of the curved front side and/or the maximum of the curved back side of the optical part and the central plane of the optical part as considered along the main optical axis. In particular, this thickness is half the central thickness of the optical part. In particular, in the non-implanted state of the intraocular lens, a distance of a ring peak from the central plane, which is consequently measured at right angles to the central plane and is consequently considered in the direction of the main optical axis, is greater than this thickness. What this particularly advantageously achieves is that particularly an upper side, especially the back side of the optical part can be positioned at a distance from a capsular bag wall, in particular at a distance from the posterior capsular bag wall, when in the eye in the implanted state.

Typically, in the circumferential direction about the main optical axis, provision is made for the two haptic rings to be arranged at the same azimuthal position with their two ring valleys. In particular, the two haptic rings, or the first ring and the second ring, are arranged at the same azimuthal position with their two ring peaks in the circumferential direction about the main optical axis.

Typically, provision is made for the rings to be arranged relative to one another such that they represent, in the region of the ring peaks, an open jaw or a jaw shape directed radially to the outside. Considered in the radial direction, this jaw has the greatest jaw opening at the radially outermost end. When considered in the circumferential direction about the main optical axis proceeding from a respective ring valley, these two rings increase in terms of radius to the other next ring valley and the distance between these two rings, considered in the direction of the main optical axis, increases continuously to the two ring peaks and then reduces again from the ring peaks to the respectively subsequent second ring valley.

In an advantageous embodiment, provision is made for the rings, by way of their respective ring valleys, to be directly connected to the optical part, in particular formed in one piece therewith, at a circumferential wall of the optical part. Provision can be made for the adjacent ring valleys of the two rings to be arranged adjacently and without overlap at this specific azimuthal position or to be formed in a manner overlapping with one another. The rings can also be designed in one piece with one another as a ring ensemble.

In an advantageous embodiment, provision can be made for the rings to be in the form of annuli in the state in which they are folded into a plane, in which then only the two-dimensional design is illustrated. When considered in this respect as a two-dimensional entity in a plane, they may also be in the form of oval rings.

Typically, at least one of the two rings is formed without interruption in the circumferential direction and hence formed in completely closed fashion. In an advantageous embodiment, provision is made for an axial distance of a ring peak of a ring from the central plane of the optical part to be greater than a distance of an arching maximum, in particular a central arching maximum, of the optical part from the central plane. As a result, the intraocular lens can also be positioned in the capsular bag such that the optical part is arranged at a distance from a capsular bag wall. In particular, this is advantageous for a back side of the optical part. Then, this back side can be arranged in the capsular bag at a distance from a posterior capsular bag wall. As a result, aqueous humor can reach between this back side and the posterior capsular bag. As a result, it is possible to avoid the migration of cells and consequently avoid opacification of the posterior capsular bag.

In particular, the intraocular lens is a posterior chamber lens for implantation into a capsular bag of an eye.

The intraocular lens proposed in this respect is foldable and can be positioned symmetrically in the capsular bag without axial displacements arising. The haptic specified in this respect can individually adapt to the spatial conditions in the capsular bag in improved fashion. As a result, it is possible to avoid unwanted changes in the position of the optic part or of the optical part of the intraocular lens. In particular, this embodiment of the haptic also achieves an improved rotational stability of the intraocular lens in the capsular bag.

In particular, the intraocular lens is formed in one piece from a polymer material.

In particular, the intraocular lens takes the form of an intraocular lens implanted in a capsular bag. It may also be referred to as a capsular bag-implanted intraocular lens in this context. In particular, it is a posterior chamber lens for implantation into a capsular bag of an eye in this context. This means that the intraocular lens is intended, especially solely, for implantation into a capsular bag of an eye.

Further features of the disclosure are apparent from the claims, the figures and the description of the figures. The features and combinations of features mentioned in the description above and the features and combinations of features mentioned in the description of the figures below and/or shown in the figures alone may be used not only in the respectively specified combination but also in other combinations, without departing from the scope of the disclosure. The disclosure shall thus also be considered to include and disclose embodiments that are not shown and elucidated explicitly in the figures, but result and can be created from separate combinations of features from the details elucidated. Disclosure shall also be considered to extend to embodiments and combinations of features that thus do not have all the features of an independent claim as originally worded. Disclosure shall additionally be considered to extend to embodiments and feature combinations, in particular by virtue of the embodiments explained above, which go beyond or depart from the feature combinations set out in the dependency references of the claims.

The concrete values indicated in the documents for parameters and indications concerning ratios of parameters or parameter values for the definition of exemplary embodiments of the eye lens should be considered to be concomitantly encompassed by the scope of the disclosure even in the context of deviations, for example on account of measurement errors, system faults, DIN tolerances, etc., which means that explanations relating to substantially corresponding values and indications should also be understood thereby.

BRIEF DESCRIPTION OF THE DRAWINGS

The disclosure will now be described with reference to the drawings wherein.

DESCRIPTION OF EXEMPLARY EMBODIMENTS

In the figures, identical or functionally equivalent elements are given the same reference symbols.

Figure 1:
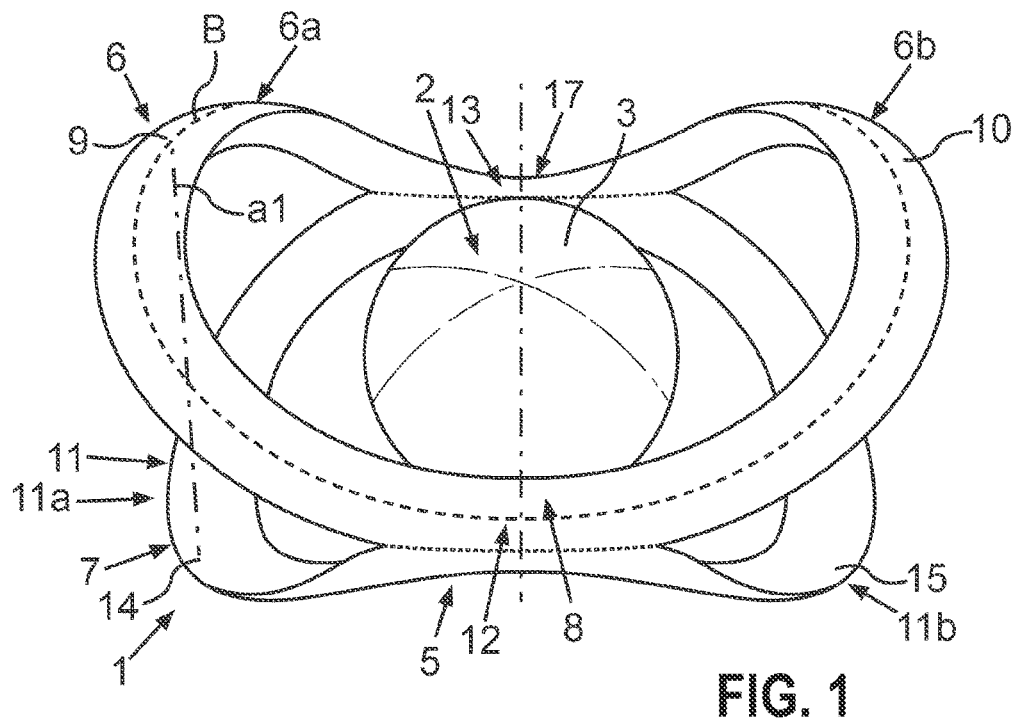
FIG. 1 shows a perspective illustration of an intraocular lens according to an exemplary embodiment of the disclosure.

FIG. 1 shows a perspective view of an exemplary embodiment of an artificial intraocular lens 1. This intraocular lens 1 is a posterior chamber lens for implantation into a capsular bag of an eye. It may therefore also be referred to as a capsular bag-implanted intraocular lens. The intraocular lens 1 includes an optical part 2. The optical part 2 is in the form of a lens. It is configured to create a defined optical imaging characteristic of the intraocular lens 1. The intraocular lens 1 has an optical axis or a main optical axis A. It passes through a front side 3 of the optical part 2 and a back side 4 of the optical part 2, centrally and in the middle of the optical part 2.

The intraocular lens 1 includes a haptic 5. In the exemplary embodiment shown, the haptic 5 is formed from two rings 6 and 7. The first ring 6 in the exemplary embodiment is elastically deformable, at least in regions. The first ring 6 has an uneven form in the circumferential direction about the main optical axis A. This means that the entire shape or the entire geometry of the first ring 6 is not arranged in a single plane. Rather, the first ring 6 is formed as a three-dimensionally shaped ring. In respect of its three-dimensional shape, the first ring 6 has exactly two ring valleys 8 and 17. Moreover, the first ring 6 has exactly two ring peaks 9 and 10. The ring valleys 8 and 17 and the ring peaks 9 and 10 should be viewed in relation to a central plane M (FIGS. 6a to 6c) of the optical part 2 in particular. This central plane M of the optical part 2 in the form of a lens extends, in particular extends centrally, through this optical part 2 and is oriented at right angles to the main optical axis A. Consequently, when considered in the direction of the main optical axis A, the two ring valleys 8 and 17 have a shorter distance from the central plane M than the ring peaks 9 and 10. In particular, in the circumferential direction, provision is made for the ring valleys 8 and 17 to be arranged 180° offset from one another about the main optical axis A. A corresponding exemplary embodiment applies to the ring peaks 9 and 10. The ring peaks 9 and 10 are formed at the same distance from the two ring valleys 8 and 17 along the longitudinal axis B of the first ring 6.

In particular, the first ring 6 has the shape of an edge ring of a saddle form. When in its position in the completed final state of the intraocular lens 1, the first ring 6 is in the form of an annulus or oval ring, which is curved about an axis that is located in the central plane M and oriented at right angles to the main optical axis A. This saddle form arises as a result. Provision can also be made for this end position of the first ring 6 to be formed as a ring-shaped cutout from a lateral wall of a hollow cylinder, with the cylinder axis of this hollow cylinder being the cylinder axis located in the central plane M and oriented at right angles to the main optical axis A.

At the circumferential side, the first ring 6 is coupled to the optical part 2 by way of its ring valleys 8 and 17. In particular, it has a direct connection to the optical part 2. The ring peaks 9 and 10 of the first ring 6 are arranged so as not to be in contact with the optical part 2. Consequently, these ring peaks 9 and 10 freely protrude to the outside in the radial direction when the radial direction in relation to the main optical axis A is considered.

As is further evident from the exemplary embodiment shown in FIG. 1, the haptic 5 has a second ring 11 in the exemplary embodiment. This second ring 11 likewise has a form without interruption in the circumferential direction about the main optical axis A and has a form which completely encircles the main optical axis A. In particular, provision is made for this second ring 11 to likewise have exactly two ring valleys 12 and 13 and two ring peaks 14 and 15. The second ring 11 is typically arranged in relation to the first ring 6 such that, in the circumferential direction about the main optical axis A, the two ring valleys 8 and 12 are arranged at the same azimuthal position and the two ring valleys 17 and 13 are also arranged at the same azimuthal position. In particular, the two rings 6 and 11 are formed and arranged such that the ring peaks 9 and 14 are arranged at the same azimuthal position and the ring peaks 10 and 15 are arranged at the same azimuthal position.

Otherwise, in respect of the shape and arrangement relative to the optical part 2, the explanations as made in relation to the first ring 6 also apply to the second ring 11.

Figure 2:
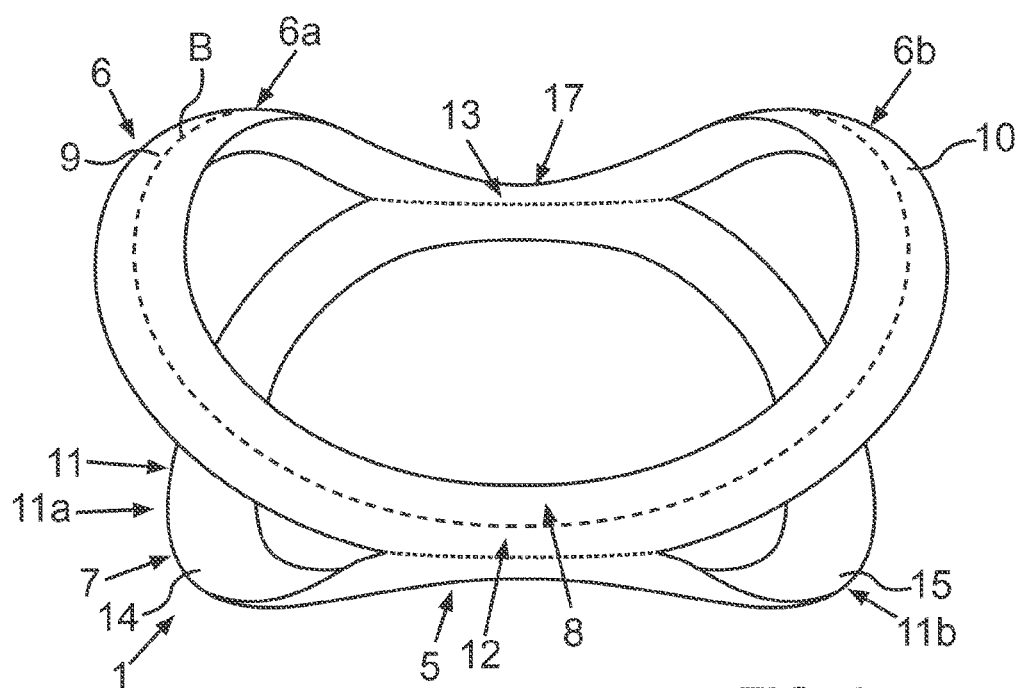
FIG. 2 shows a perspective illustration of a haptic for an intraocular lens according to an exemplary embodiment of the disclosure.

The haptic 5 of the intraocular lens 1 without the optical part 2 is shown in a perspective illustration in FIG. 2. In this case, the haptic 5 with the two rings 6 and 7 is formed in one piece. The dashed separation lines should only be understood in this case as auxiliary lines that specify the respective geometry of the rings 6 and 7. The rings 6 and 7 may also have a separate embodiment.

Figure 3:
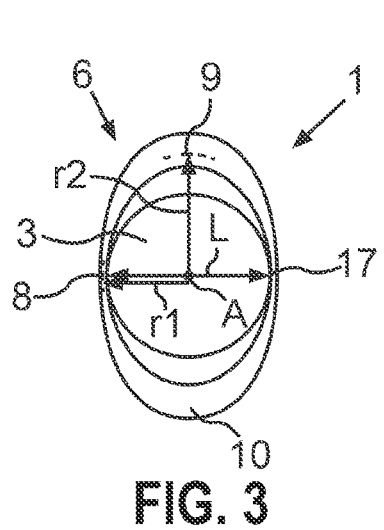
FIG. 3 shows a schematic illustration of the intraocular lens shown in FIG. 1 in a plan view in the direction of the main optical axis of the intraocular lens.

From a plan view, which is shown schematically in FIG. 3 in exemplary fashion and in the case of which the view is of the intraocular lens 1 in the direction of the main optical axis A, it is evident that the ring valleys 8 and 17 of the first ring 6 are arranged at a first radius r1 with respect to the main optical axis A. This radius r1 is smaller than a radius r2. This second radius r2 represents the radial distance of the ring peaks 9 and 10 from the main optical axis A. In the radial direction, the ring peaks 9 and 10 of the first ring 6 are consequently further away from the main optical axis A than the ring valleys 8 and 17. The same applies to the ring valleys 12 and 13 in comparison with the ring peaks 14 and 15 of the second ring 11.

In particular, provision is made for the first ring 6 to have a first ring portion 6a, which extends from the first ring valley 8 over the first ring peak 9 and up to the second ring valley 17. The curvature or direction of curvature of this first ring portion 6a is directed radially to the outside in relation to the main optical axis A. Consequently, in the projected view according to FIG. 3, the first ring portion 6a represents a U-arch. It extends from a circumferential point of the optical part 2 to a further circumferential point of the optical part 2 which is offset from the former by 180° in this respect. The corresponding statement applies to a second ring portion 6b of the first ring 6. Together, the two ring portions 6a and 6b yield the first ring 6. The same applies to a first ring portion 11a and a second ring portion 11b of the second ring 11.

A clear width L which extends in a straight line between the ring valleys 8 and 17 and runs through the main optical axis A measures at least 90 percent, in particular at least 100 percent of the diameter of the optical part 2. The same applies to a clear width between the ring valleys 12 and 13.

In respect of its curvature with respect to the main optical axis A, this first ring portion 6a is directed radially to the outside. The same applies to the second ring portion 6b. A corresponding statement applies to the curvatures or directions of curvature of the ring portions 11a and 11b.

In a non-implanted basic state of the intraocular lens 1, the ring peaks 9 and 14 have a distance a1, which is measured in the direction of the main optical axis A. This distance a1 is larger than an optionally present distance between the ring valleys 8 and 12 and/or the ring valleys 17 and 13 as measured in the direction of the main optical axis A. In particular, a corresponding distance a1 is also formed between the ring peaks 10 and 15. When considered in the circumferential direction about the main optical axis A, a distance between the two rings 6 and 11 varies between a minimum or a distance of 0 at the ring valleys 8, 12 and 17, 13 and a respective maximum, which is formed by the distances a1 between the ring peaks 9, 14 and/or the ring peaks 10, 15.

Moreover, provision is made for the ring peaks 9 and 10 of the first ring 6 to have a greater distance from the central plane M in the optical part 2 than the ring valleys 8 and 17 when considered in the direction of the main optical axis A. In particular, this distance is half of the distance a1. In particular, a corresponding statement applies to the distances of the ring peaks 14 and 15 from this central plane M, in particular in relation to the ring valleys 12 and 13.

In particular, the two rings 6 and 11 are formed symmetrically with respect to the central plane M.

Figure 4:
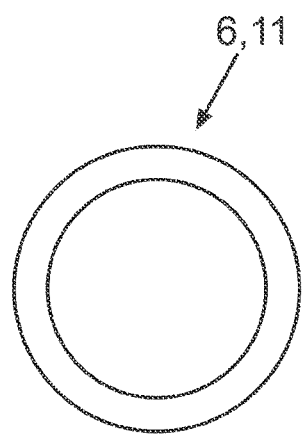
FIG. 4 shows a schematic illustration of a ring of the haptic in a two-dimensional basic shape, in which the ring is an annulus.
Figure 5:
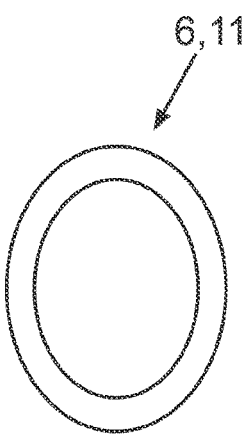
FIG. 5 shows an illustration in accordance with FIG. 4, in which a ring is represented as an oval ring in a basic shape according to a further exemplary embodiment of the disclosure.

FIG. 4 shows an exemplary embodiment of a first ring 6. This ring 6 is illustrated in the plane of the drawing and is correspondingly folded open in comparison with FIG. 1, and therefore illustrated in planar fashion. It has the shape of an annulus in this folded-open plane representation. In this respect, FIG. 5 shows an alternative embodiment of the first ring 6 in this plane of the drawing, which ring is hence shown in a folded-open state in comparison with the final position of an intraocular lens 1 and is consequently shown in a two-dimensional representation. In this case, this folded-open basic shape can be an oval ring in a plan view. Corresponding shapes, as shown in the two-dimensional, folded-open basic shape of the first ring 6 in FIG. 4 and FIG. 5, may also be formed for the second ring 11.

Figures 6A, 6B, 6C:
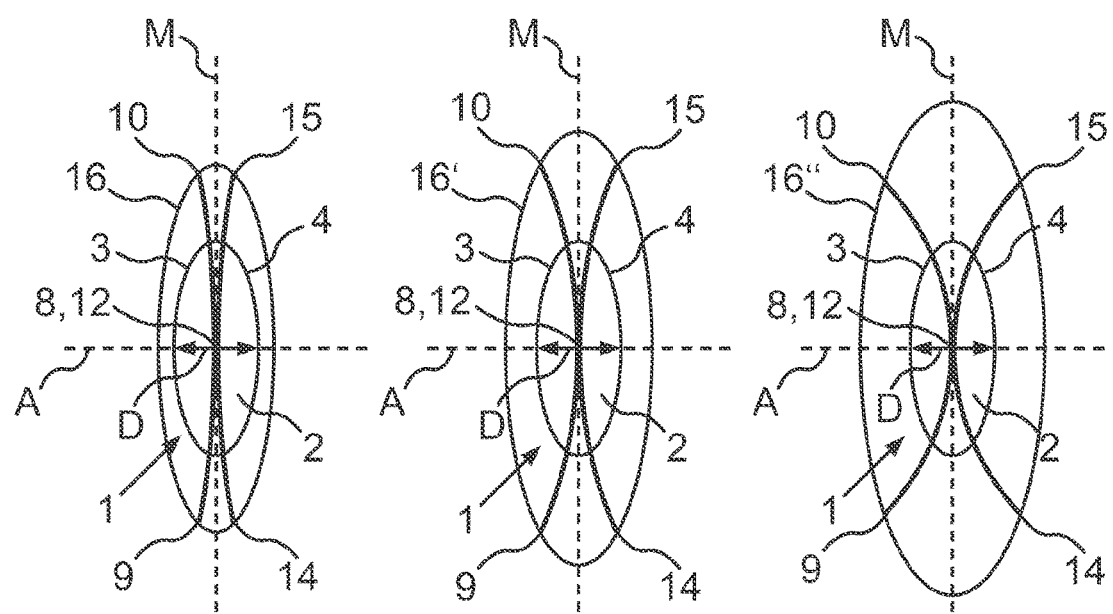
FIG. 6A shows a schematic illustration of an intraocular lens which is implanted in a capsular bag according to an exemplary embodiment of the disclosure.
FIG. 6B shows an illustration in accordance with FIG. 6A, in which the intraocular lens is implanted in a capsular bag that is larger than the one in FIG. 6A.
FIG. 6C shows an illustration in accordance with FIGS. 6A and 6B, in which the intraocular lens is implanted in an even larger capsular bag.

An implanted state of the intraocular lens 1 in a capsular bag 16 is shown in a schematic illustration in FIG. 6A. The capsular bag 16 which is relatively small in this case requires the ring peaks 9, 10, 14, and 15 to move toward one another quite significantly, and said peaks are consequently elastically deformed in this respect. The optical part 2 has a central thickness D. This central thickness D is measured along the main optical axis A and represents the greatest thickness of the optical part 2. A thickness measured between the front side 3 and the central plane M along the main optical axis A represents half this central thickness D. In particular, in the non-implanted state of the intraocular lens 1, a distance of a ring peak 9, 10 from the central plane M is larger than this distance D/2 when considered in the direction of the main optical axis A.

In particular, this exemplary embodiment also allows the optical part 2 of the intraocular lens 1 to be arranged at a distance from the capsular bag walls, in particular a posterior capsular bag wall, when said intraocular lens 1 is in the implanted state in the capsular bag 6. Hence, aqueous humor can reach between a back side 4 and the posterior capsular bag wall of the capsular bag 16.

A further exemplary embodiment of the implanted state of the intraocular lens 1 in a capsular bag 16' is shown in FIG. 6B. This capsular bag 16' differs from the capsular bag 16 in terms of size and/or shape. On account of the elasticity and specific shape of the haptic 5, positionally secure and/or rotationally stable and/or tilt-free positioning is also facilitated therein. A further illustration of an implanted state of the intraocular lens 1 in a capsular bag 16" that differs yet again in this respect is schematically shown in FIG. 6C.

It is understood that the foregoing description is that of the exemplary embodiments of the disclosure and that various changes and modifications may be made thereto without departing from the spirit and scope of the disclosure as defined in the appended claims.

What is claimed is:

1. An intraocular lens, comprising:
   a single optical part having a front side and a back side;
   a haptic coupled to the single optical part;
   the intraocular lens defining a main optical axis which passes through the front side and the back side of the single optical part;
   the haptic including a first haptic part which is in a form of a first ring and encircles the single optical part, and at least one second haptic part which is in the form of a second ring and encircles the single optical part and which is elastically movable relative to the first haptic part;
   at least one of the first and second rings having an uneven form in a circumferential direction about the main optical axis;
   the first ring having exactly two first ring valleys and exactly two first ring peaks;
   the second ring having exactly two second ring valleys and exactly two second ring peaks;
   one ring valley of the exactly two first ring valleys and one ring valley of the exactly two second ring valleys being arranged at a same first azimuthal position in a circumferential direction about the main optical axis and another ring valley of the exactly two first ring valleys and another ring valley of the exactly two second ring valleys being arranged at a same second azimuthal position in the circumferential direction about the main optical axis such that the first ring and the second ring are in contact with one another at the same first and second azimuthal positions.

2. The intraocular lens as claimed in claim 1, wherein at least one of the first and second rings with the exactly two ring valleys and the exactly two ring peaks has a shape of an edge ring of a saddle form.

3. The intraocular lens as claimed in claim 1, wherein the at least one of the first and second rings merges with the single optical part with its ring valleys along a circumferential side and its ring peaks arranged so as not to be in contact with the single optical part.

4. The intraocular lens as claimed in claim 3, wherein the ring valleys are arranged at a first radius with respect to the main optical axis in a projected view in a direction of the main optical axis and the ring peaks are arranged at a second radius which is comparatively larger than the first radius in the projected view.

5. The intraocular lens as claimed in claim 1, wherein the at least one of the first and second rings with the exactly two ring valleys and the exactly two ring peaks has a first ring portion which extends from the first ring valley over a first ring peak and up to a second ring valley, and a clear width of the first ring portion as measured between the ring valleys being at least 90% of a diameter of the single optical part.

6. The intraocular lens as claimed in claim 1, wherein the at least one of the first and second rings with the exactly two ring valleys and exactly two ring peaks has a first ring portion which extends from the first ring valley over a first ring peak and up to a second ring valley, a curvature of the first ring portion being directed radially to the outside in relation to the main optical axis.

7. The intraocular lens as claimed in claim 1, wherein the single optical part defines a central plane, and
   wherein the ring peaks have a larger distance from the central plane of the single optical part than the ring valleys when considered parallel to the main optical axis.

8. The intraocular lens as claimed in claim 7, wherein the first ring has a same shape as the second ring and the first and second rings are arranged symmetrically in relation to the central plane of the single optical part.

9. The intraocular lens as claimed in claim 8, wherein the first and second rings, with their respective ring valleys, are directly connected to the single optical part at a circumferential wall of the single optical part.

10. The intraocular lens as claimed in claim 8, wherein the first and second rings, are formed in one piece with the single optical part.

11. The intraocular lens as claimed in claim 1, wherein the intraocular lens is a posterior chamber lens for implantation into a capsular bag of an eye.

* * * * *

UNITED STATES PATENT AND TRADEMARK OFFICE
CERTIFICATE OF CORRECTION

PATENT NO. : 12,364,592 B2  
APPLICATION NO. : 17/683172  
DATED : July 22, 2025  
INVENTOR(S) : Stephanie Mueller Page 1 of 1

It is certified that error appears in the above-identified patent and that said Letters Patent is hereby corrected as shown below:

On the Title Page

Item (56) U.S. Patent Documents:
Replace "2015/0142108 A1 5/2015 Akura" with "2015/0142108 A1 5/2015 Akura et al."

Signed and Sealed this
Twenty-third Day of September, 2025

John A. Squires
*Director of the United States Patent and Trademark Office*